United States Patent [19]

Boden

[11] 4,395,425
[45] Jul. 26, 1983

[54] USE OF PRINS REACTION PRODUCTS OF DIISOAMYLENE DERIVATIVES TO AUGMENT OR ENHANCE THE AROMA OR TASTE OF FOODSTUFFS

[75] Inventor: Richard M. Boden, Monmouth Beach, N.J.

[73] Assignee: International Flavors & Fragrances Inc., New York, N.Y.

[21] Appl. No.: 391,588

[22] Filed: Jun. 24, 1982

Related U.S. Application Data

[62] Division of Ser. No. 267,850, May 28, 1981, Pat. No. 4,359,412.

[51] Int. Cl.³ .............................................. A23L 1/226
[52] U.S. Cl. ...................................... 426/3; 426/534; 426/536
[58] Field of Search ........................... 426/534, 536, 3

[56] References Cited
U.S. PATENT DOCUMENTS
4,359,412 11/1982 Boden .............................. 426/536 X Primary Examiner—Joseph M. Golian
Attorney, Agent, or Firm—Arthur L. Liberman

[57] ABSTRACT

Described for use in augmenting or enhancing the aroma or taste of foodstuffs is the genus of compounds defined according to the structure:

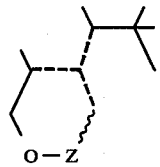

wherein one of the dashed lines represents a carbon-carbon double bond and each of the other of the dashed lines represent carbon-carbon single bonds; wherein the wavy line represents a carbon-carbon single bond or no bond; wherein when the wavy line represents a carbon-carbon single bond, Z represents methylene and when the wavy line represents no bond, Z represents hydrogen or $C_2$-$C_4$ acyl prepared according to a Prins reaction between diisoamylene defined according to the structure:

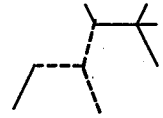

wherein one of the dashed lines represents a carbon-carbon double bond and each of the other of the dashed lines represent carbon-carbon single bonds or one of the structures:

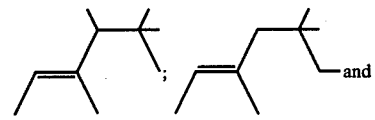

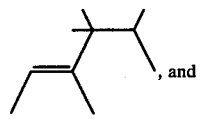

formaldehyde of a formaldehyde source such as trioxane or paraformaldehyde in the presence of an acyl anhydride and an acid catalyst.

8 Claims, No Drawings

USE OF PRINS REACTION PRODUCTS OF DIISOAMYLENE DERIVATIVES TO AUGMENT OR ENHANCE THE AROMA OR TASTE OF FOODSTUFFS

This application is a divisional of application for U.S. Letters Patent Ser. No. 267,850 filed on May 28, 1981, now U.S. Pat. No. 4,359,412 issued on Nov. 16, 1982.

BACKGROUND OF THE INVENTION

The instant invention relates to compounds having the genus:

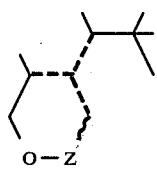

wherein one of the dashed lines represents a carbon-carbon double bond and each of the other of the dashed lines represent carbon-carbon single bonds; wherein the wavy line ∽ represents a carbon-carbon single bond or no bond; wherein when the wavy line represents a carbon-carbon single bond, Z represents methylene and when the wavy line represents no bond, Z represents hydrogen or $C_2$-$C_4$ acyl and includes compounds defined according to the structure:

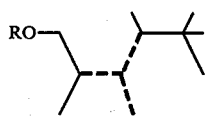

wherein R represents hydrogen or $C_2$-$C_4$ acyl and compounds defined according to the structure:

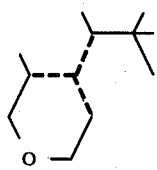

wherein in each of the compound genera, one of the dashed lines represents a carbon-carbon double bond and each of the other of the dashed lines represent carbon-carbon single bonds.

Inexpensive chemical compounds which can provide intense and long-lasting woody, ionone-like, fruity, floral, amber, cedarwood, vanoris-like, peach, coriander-like, citrusy, oriental and minty aroma nuances are desirable in the art of perfumery. Many of the natural materials which provide such fragrances and contribute such desired nuances to perfumery compositions are high in cost, unobtainable at times, vary in quality from one batch to another and/or are generally subject to the usual variations of natural products.

There is, accordingly, a continuing effort to find synthetic materials which will replace, enhance or augment the fragrance notes provided by natural essential oils or compositions thereof. Unfortunately, many of the synthetic materials either have the desired nuances only to a relatively small degree, or they contribute undesirable or unwanted odor to the compositions.

In addition, there is a continuing search for food flavor compositions which can vary, fortify, modify, enhance, augment or otherwise improve the flavor and/or aroma of foodstuffs, medicinal products, toothpastes, chewing gums and chewing tobaccos. To be satisfactory, such compositions should be stable, non-toxic and blendable with other ingredients to provide their own unique flavor and aroma nuances without detracting from the co-ingredients of the formulations in which they are used. Preferably, such compositions should be naturally occurring or present in natural foodstuffs so that their ingestible safety can be readily recognized. These materials should be capable of being synthesized in a simple and economical manner. Thus, the need for safe flavors in the raisin and rum flavor area is well known particularly in the ice cream, chewing tobacco and yogurt flavor areas. More specifically, there is a need for the development of non-toxic materials which can replace natural materials not readily available, having sweet, floral, coriander-like, fruity, cedarwood-like and oriental aroma characteristics with sweet, vanilla-like, floral, fruity, coriander-like, cedarwood and raisin-like flavoring characteristics.

In the tobacco flavoring art (pertaining to tobaccos and substitute tobaccos), there is a considerable need for substituents having oriental, fruity, rum-like, and Turkish tobacco-like aroma and taste nuances both prior to and on smoking in the main stream and in the side stream. Specifically described herein are materials having such an organoleptic profile but which are stable with respect to time.

The instant invention provides the foregoing, which the prior art has heretofore failed to provide. Furthermore, the compounds defined according to the genus:

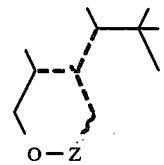

have unobvious, unexpected and advantageous organoleptic properties (wherein one of the dashed lines represents a carbon-carbon double bond and each of the other of the dashed lines represent carbon-carbon single bonds; wherein the wavy line ∽ represents a carbon-carbon single bond or no bond; wherein when the wavy line represents a carbon-carbon single bond, Z represents methylene and when the wavy line represents no bond, Z represents hydrogen or $C_2$-$C_4$ acyl).

The compounds defined according to the genus:

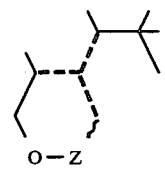

wherein one of the dashed lines represents a carbon-carbon double bond and each of the other of the dashed lines represent carbon-carbon single bonds; wherein the wavy line ⌇ represents a carbon-carbon single bond or no bond; wherein when the wavy line represents a carbon-carbon single bond, Z represents methylene and when the wavy line represents no bond, Z represents hydrogen or $C_2$-$C_4$ acyl are prepared according to the "Prins" reaction, which reaction, basically, involves the reaction of an olefinic double bond-containing compound with formaldehyde or a formaldehyde precursor or formaldehyde source such as trioxane, paraformaldehyde or formalin.

Perfumery compounds are known to have been produced using the Prins reaction. Thus, the paper entitled "The Olefin-Aldehyde Condensation/The Prins Reaction" by Arundale and Mikeska, Chem. Reviews, 51, 505–55 1952, discloses the reaction to form Nopol acetate, thusly:

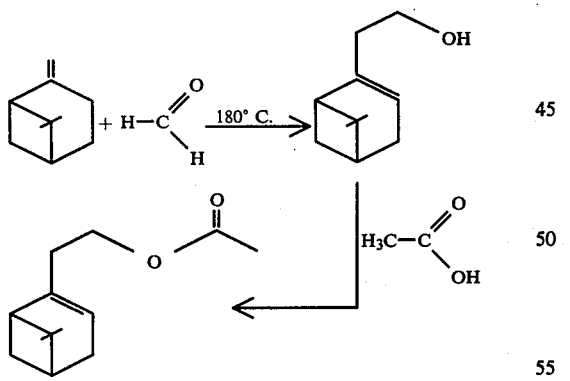

wherein in the reaction, when glacial acetic acid is added to the reaction mass, the Nopol acetate is formed; yet without the use of glacial acetic acid, Nopol itself is formed.

U.S. Pat. No. 4,100,110 issued on July 11, 1978 (Class 252, subclass 522) discloses compounds for use in perfumery which are obtained by performing a Prins reaction on longifolene including primary and secondary alcohols, their esters and corresponding aldehydes and ketones. Specifically, in Example 1, column 7 of U.S. Pat. No. 4,100,110 discloses the preparation of compounds having the structures:

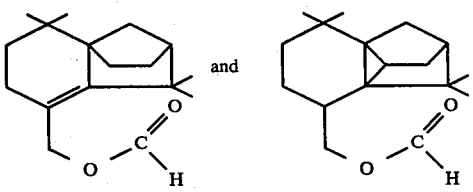

for use in perfumery as a result of their cedarwood-vetiver aroma.

The compounds of the prior art and processes of the prior art are different in kind and yield materials having organoleptic properties different in kind from the compounds of the instant invention.

RELATED PATENT APPLICATIONS

| Serial Number | Filing Date | Title |
|---|---|---|
| 233,861 (now U.S. Letters Pat. No. 4,304,689) | February 12, 1981 | "ALIPHATIC $C_{11}$ BRANCHED CHAIN ALDEHYDES AND ALCOHOLS, PROCESS FOR PREPARING SAME AND USES THEREOF IN ARGUMENTING OR ENHANCING THE AROMA OF PERFUMES, COLOGNES AND/OR PERFUMED ARTICLES" |
| 212,887 (now U.S. Letters Pat. No. 4,318,934) | December 4, 1980 | "BRANCHED CHAIN OLEFINIC ALCOHOLS, THIOLS, ESTERS AND ETHERS, ORGANOLEPTIC USES THEREOF, PROCESSES FOR PREPARING SAME AND INTERMEDIATES THEREFOR" |
| U.S. Letters Pat. No. 4,336,164 | April 9, 1981 | "BRANCHED CHAIN OLEFINIC ALCOHOLS, THIOLS, ESTERS AND ESTERS, ORGANOLEPTIC USES THEREOF, PROCESSES FOR PREPARING SAME AND INTERMEDIATES THEREFOR" |

THE INVENTION

The present invention provides compounds defined according to the generic structure:

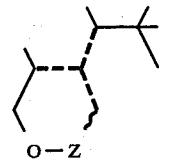

wherein one of the dashed lines represents a carbon-carbon double bond and each of the other of the dashed lines represent carbon-carbon single bonds; wherein the wavy line ⌇ represents a carbon-carbon single bond or no bond at all; when the wavy line represents a carbon-carbon single bond, Z represents —$CH_2$— and when the wavy line represents no bond at all, Z represents hydrogen, or $C_2$-$C_4$ acyl. Thus, more specifically, when the wavy line represents a carbon-carbon single bond, the genus is more specific in the structure:

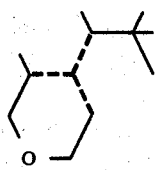

wherein one of the dashed lines represents a carbon-carbon double bond and each of the other of the dashed lines represent carbon-carbon single bonds; and where the wavy line represents no bond at all, the genus is represented by the structure:

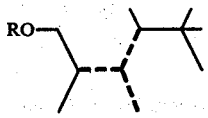

wherein R represent hydrogen or $C_2$–$C_4$ acyl and one of the dashed lines represents a carbon-carbon double bond and each of the other of the dashed lines represent carbon-carbon single bonds.

Collectively, the genus defined according to the structure:

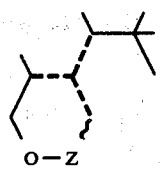

wherein the dashed lines, wavy line and the Z are defined as above, is called "one or more Prins reaction products".

The Prins reaction products of our invention produced according to the process of our invention are capable of augmenting or enhancing sweet, floral, coriander-like, fruity, cedarwood and oriental aroma characteristics and sweet, vanilla-like, floral, fruity, coriander-like, cedarwood-like and raisin taste characteristics of foodstuffs, foodstuff flavors, chewing gums, chewing gum flavors, chewing tobaccos, chewing tobacco flavors, medicinal products, medicinal product flavors, toothpastes and toothpaste flavors.

The Prins reaction products of our invention as well as mixtures thereof are also capable of modifying or enhancing the aroma characteristics of perfume compositions, colognes and perfumed articles (including soaps, nonionic, anionic, cationic and zwitterionic detergents and fabric softener articles) by imparting thereto woody, ionone-like, fruity, floral, amber, cedarwood-like, vanoris-like, peach, coriander-like, oriental, citrusy and minty aroma nuances, thus fulfilling a need in the field of perfumery.

In tobacco, tobacco flavoring, substitute tobacco and substitute tobacco flavoring compositions, the Prins reaction products of our invention produced according to the process of our invention impart oriental, fruitwood-like, rum-like, and Turkish tobacco-like aroma and taste nuances to smoking tobacco and substitute smoking tobaccos prior to and on smoking in both the main stream and the side stream.

The Prins reaction is carried out on diisoamylene with formaldehyde or a formaldehyde precursor such as formalin or paraformaldehyde in the presence of or in the absence of an acyl anhydride and in the presence of an acid catalyst; either a Lewis acid such as borontrifluoride etherate or stannic chloride or the like, or a protonic acid such as sulfuric acid or phosphoric acid.

Depending on whether an acyl anhydride is used or not; and depending on whether a protonic acid or a Lewis acid catalyst is used; and depending upon whether formaldehyde or trioxane or paraformaldehyde is used as a precursor reactant, the resulting product encompassed within the generic structure:

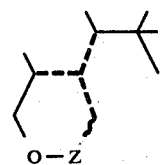

wherein one of the dashed lines represents a carbon-carbon double bond and each of the other of the dashed lines represent carbon-carbon single bonds; wherein the wavy line~represents a carbon-carbon single bond or no bond; wherein when the wavy line represents a carbon-carbon single bond, Z represents methylene and when the wavy line represents no bond, Z represents hydrogen or $C_2$–$C_4$ acyl, will be different; that is, it will be either one of the compounds encompassed by the generic structure:

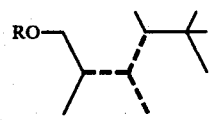

wherein R represents hydrogen or wherein R represents $C_2$–$C_4$ acyl or it will be one of the generic structures defined according to the structure:

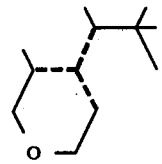

wherein one of the dashed lines represents a carbon-carbon double bond and wherein each of the other of the dashed lines represent carbon-carbon single bonds.

With respect to the diisoamylene precursor, "diisoamylene" is a dimer of isoamylene wherein the dimerization takes place in the presence of acid. "Diisoamylene" is indicated to be synthesized in the following references:

(i) Murphy & Lane, Ind. Eng. Chem., Prod. Res. Dev., Vol. 14, No. 3, 1975 p. 167 (title: Oligomerization of 2-Methyl-2-Butene in Sulfuric Acid and Sulfuric-Phosphoric Acid Mixtures).

(ii) Whitmore & Mosher, Vol. 68, J. Am. Chem. Soc., February, 1946, p. 281 (Title: The Depolymerization of 3,4,5,5-Tetramethyl-2-hexane and 3,5,5,-Trimethyl-2- heptene in Relation to the Dimerization of Isoamylenes).

(iii) Whitmore & Stahly, Vol. 67, J. Am. Chem. Soc., December, 1945, p. 2158 (Title: The Polymerization of Olefins. VIII The Depolmerization of Olefins in Relation to Intramolecular Rearrangements. II).

(iv) U.S. Pat. No. 3,627,700, issued on Dec. 14, 1971, (Zuech).

(v) U.S. Pat. No. 3,538,181, issued on Nov. 3, 1970 (Banks).

(vi) U.S. Pat. No. 3,461,184, issued on Aug. 12, 1969 (Hay, et al).

(vii) Gurwitsch, Chemische Berichte, 1912, Vol. 2, p. 796 (Production of Di-isoamylene from Iosamylene Using Mercury Acetate Catalyst).

United Kingdom Pat. No. 796,130 published on June 4, 1958 discloses the synthesis of polyalkylindanes by means of, interalia, reacting alpha-methylstyrene with trimethylethane (2-methyl-butane-2) in the presence of an acid catalyst such as, sulfuric acid or boron trifluoride etherate. It is further indicated that such compounds are useful intermediates in the production of perfumery compounds. Apparently, however, the more volatile diisoamylenes produced as sideproducts in the reaction of 2-methyl-butene-2 with alpha-methylstyrene have heretofore been discarded.

The "formaldehyde" precursor is shown as having the structure:

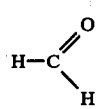

yet, in place of formaldehyde itself, trioxane having the structure:

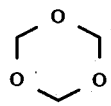

or paraformaldehyde having the structure:

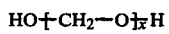

wherein X is an integer of from 2 up to 40 may be used in place of formaldehyde. Whenever formaldehyde having the structure:

is shown in a reaction with quotation marks around it thusly, it is intended that this particular term mean either formaldehyde itself or trioxane or paraformaldehyde or formalin or any other form of formaldehyde.

When the Prins reaction of my invention is carried out using paraformaldehyde as a precursor with the diisoamylene and using a Lewis acid catalyst such as borontrifluoride etherate, stannic chloride, zinc chloride, zinc bromide, diethyl aluminum chloride, aluminum diethyl chloride, or the like, and in the presence of an acyl anhydride having the structure:

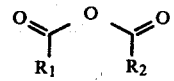

wherein $R_1$ and $R_2$ may be the same or different and each represents $C_1$–$C_3$ alkyl, a compound having the structure:

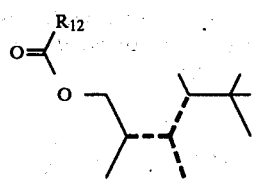

wherein $R_{12}$ represents $R_1$ or $R_2$ and one of the dashed lines in the resulting material is a carbon-carbon double bond and each of the other of the dashed lines are carbon-carbon single bonds.

When the reaction is carried out using formaldehyde per se, rather than paraformaldehyde, however, even in the presence of a Lewis acid catalyst such as stannic chloride or boron trifluoride etherate, and even in the presence of an acyl anhydride having the structure:

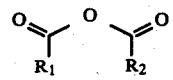

the compound that is formed is an alcohol defined according to the generic structure:

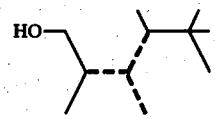

wherein one of the dashed lines represents a carbon-carbon double bond and each of the other of the dashed lines represent carbon-carbon single bonds.

When the reaction is carried out using formaldehyde alone, in the absence of an acyl anhydride, the reaction product is also the alcohol defined according to the structure:

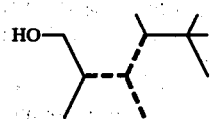

however, the alcohol at this particular point is formed in yields lower than that when compared to the reaction carried out first forming the ester having the structure:

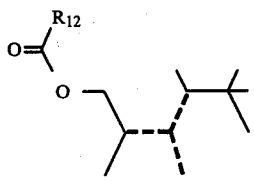

and then hydrolyzing this ester having the structure:

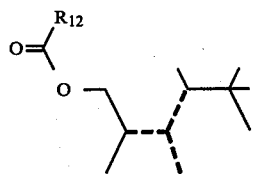

to form the alcohol having the structure:

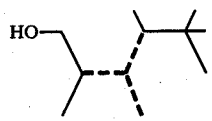

wherein in each of the molecules, one of the dashed lines represents a carbon-carbon double bond and each of the other of the dashed lines represent carbon-carbon single bonds.

Once the ester having the generic structure:

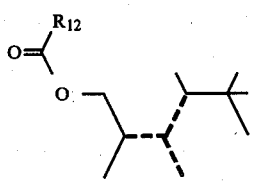

is formed, wherein $R_{12}$ represents $R_1$ and $R_2$ and each are the same or different and each represents $C_1-C_3$ alkyl, this material may be hydrolyzed in the presence of base to form, in relatively high yields, a mixture of compounds defined according to the structure:

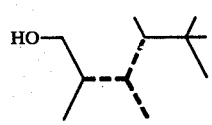

However, when using in place of a Lewis acid catalyst, a protonic acid catalyst such as sulfuric acid or phosphoric acid, even when using an acyl anhydride having the structure:

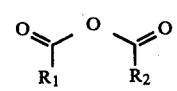

the reaction product rather than having the structure:

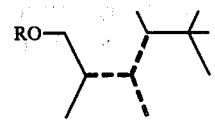

wherein R is hydrogen or $C_2-C_4$ acyl, is cyclic in nature having the structure:

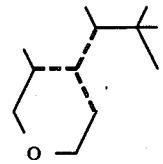

whereby 2 moles of formaldehyde react with 1 mole of diisoamylene to form such molecules having the structure:

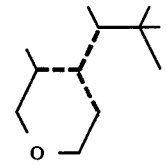

rather than the case where 1 mole of formaldehyde reacts as is the case in the presence of the Lewis acid catalyst forming the structure:

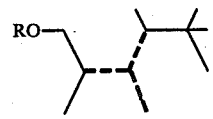

Where one of the compounds defined according to the structure:

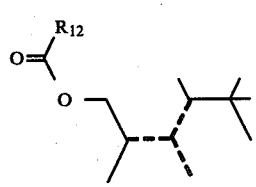

is formed wherein $R_{12}$ represents $C_1-C_3$ alkyl and one of the dashed lines represents a carbon-carbon double bond and the other of the dashed lines represent carbon-carbon single bonds, this compound may be used "as is" for its organoleptic properties or it may be hydrolyzed in the presence of base to form one of the compounds defined according to the genus:

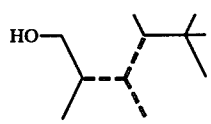

wherein one of the dashed lines represents a carbon-carbon double bond and the other of the dashed lines represent carbon-carbon single bonds. Again, this compound can be used "as is" for its organoleptic properties or it may be re-esterified with another alkanoic acid anhydride having the structure:

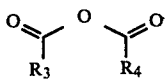

wherein $R_3$ and $R_4$ are the same or different and each represents $C_1-C_3$ alkyl whereby one of the compounds defined according to the structure:

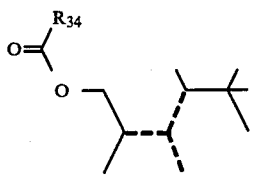

is formed wherein $R_{34}$ is $C_1-C_3$ alkyl and one of the dashed lines represents a carbon-carbon double bond and each of the other of the dashed lines represent carbon-carbon single bonds.

Thus, the reaction sequences encompassed by my invention are as follows:

(a) The reaction of the alkanoic acid anhydride with diisoamylene and formaldehyde in the presence of a Lewis acid catalyst to form the $C_{11}$ alcohol ester thusly:

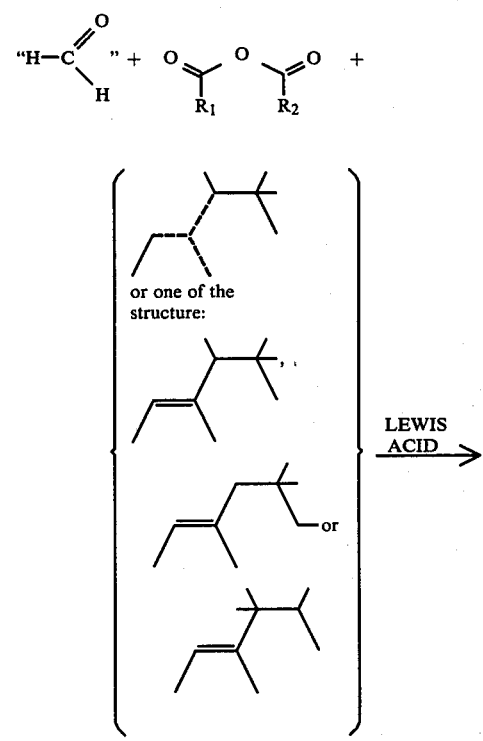

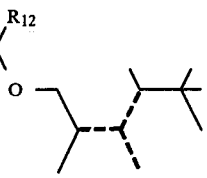

wherein $R_1$ and $R_2$ are the same or different and each represents $C_1-C_3$ alkyl; wherein $R_{12}$ is $R_1$ or $R_2$ and represents $C_1-C_3$ alkyl and wherein one of the dashed lines represents a carbon-carbon double bond and each of the other of the dashed lines represent carbon-carbon single bonds;

(b) The hydrolysis reaction:

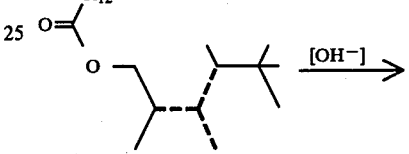

wherein $R_{12}$ and the dashed lines are defined as above;

(c) The re-esterification reaction:

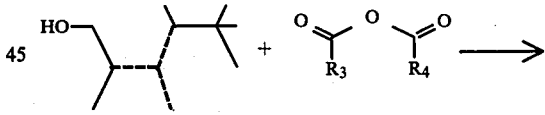

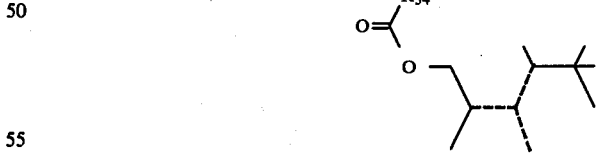

wherein one of the dashed lines represents a carbon-carbon double bond and each of the other of the dashed lines represent carbon-carbon single bonds and wherein $R_3$ and $R_4$ are the same or different $C_1-C_3$ alkyl; and wherein $R_{34}$ is $R_3$ or $R_4$ and represents $C_1-C_3$ alkyl; and (d) The reaction of the diisoamylene with formaldehyde and an alkanoic acid anhydride in the presence of a protonic acid catalyst thusly:

{ 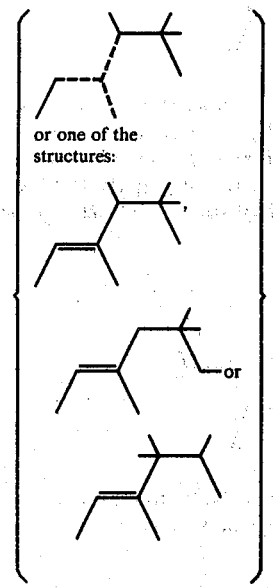 or one of the structures: } +

{ 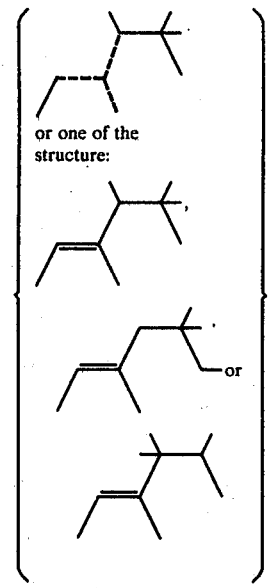 or one of the structure: } →[LEWIS ACID]

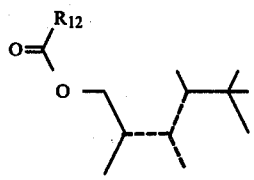

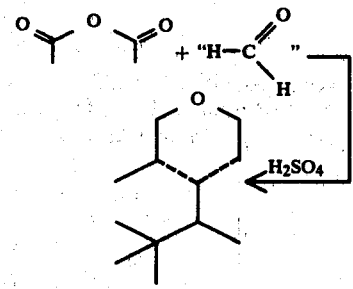

the Lewis acid may be borontrifluoride etherate, stannic chloride, zinc chloride, zinc bromide, ethyl aluminum dichloride, diethyl aluminum chloride, or aluminum trichloride. $R_1$ and $R_2$ may be the same or different and each represents $C_1$-$C_3$ alkyl such as methyl, ethyl, isopropyl or n-propyl. The formaldehyde used may be and is preferably paraformaldehyde, however, trioxane may also be used. Formaldehyde itself or formalin should not be used if the ester is attempted to be formed since low yields of alcohol will be formed rather than the ester in accordance with the reaction:

wherein one of the dashed lines represents a carbon-carbon double bond and the other of the dashed lines represent carbon-carbon single bonds.

In the esterification reaction:

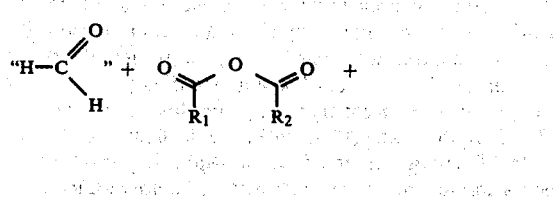

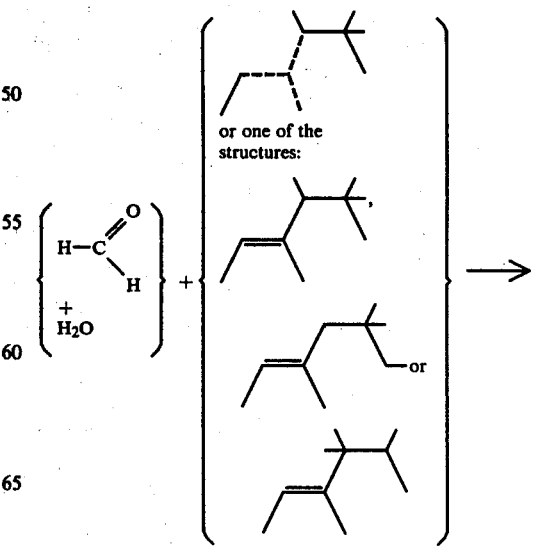

-continued

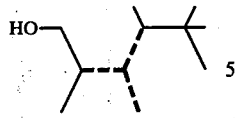

Trioxane has the structure:

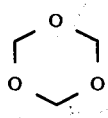

Paraformaldehyde is indicated by the structure:

$$HO\text{-}(CH_2\text{-}O)_xH$$

The mole ratio of diisoamylene:formaldehyde (as paraformaldehyde or as trioxane) may vary from about 1:2 up to about 2:1 with a preferred mole ratio of about 1:1. The mole ratio of acyl anhydride:diisoamylene may vary from about 1:1 up to about 2:1 acyl anhydride:diisoamylene with a preferred mole ratio of 1.4–1.5:1 of acyl anhydride:diisoamylene. The concentration of diisoamylene in the reaction mass is preferably from about 1 mole per liter up to about 5 moles per liter.

The concentration of Lewis acid in the reaction mass may vary from about 0.01 moles per liter up to about 0.5 moles per liter.

The reaction temperature may vary from about 50° C. up to about 150° C. depending on the pressure above the reaction mass and depending upon the time desired to complete the reaction for a given particular yield. When higher temperatures are used, the time of reaction required for completion is shorter, however, the yield is lower and the quantity of by-product formed is greater. The most desirable reaction temperature varies between 80° and 110° C. It is most preferable to carry out the reaction at atmospheric pressure. Higher reaction pressures or lower reaction pressures do not give rise to a higher yield or higher conversion rate.

At the end of the reaction, the reaction mass may be "worked-up" in the usual way by means of, for example, distillation or chromatographic separation, e.g. commercial high-pressure liquid chromatography.

In carrying out the hydrolysis reaction to form the $C_{11}$ unsaturated alcohol thusly:

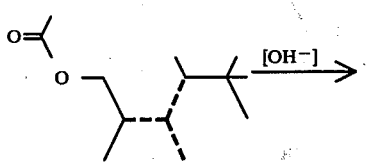

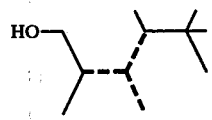

the mole ratio of ester having the structure:

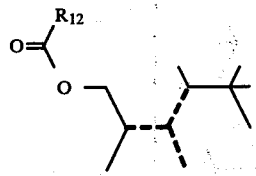

to alkali metal hydroxide, e.g., potassium hydroxide, sodium hydroxide or lithium hydroxide, may vary from about 1:2 up to about 2:1 with an excess of alkali metal hydroxide being preferred. That is, it is preferred that the mole ratio of alkali metal hydroxide:ester having the structure:

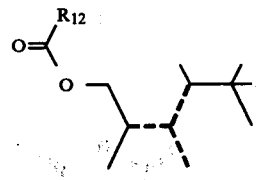

be about 2:1. It is preferred that the hydrolysis reaction to form the compound having the structure:

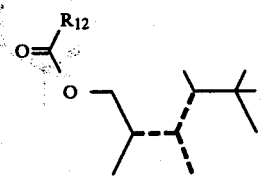

be carried out using highly concentrated base, e.g., from about 30% up to about 50% concentration. Concentration of ester having the structure:

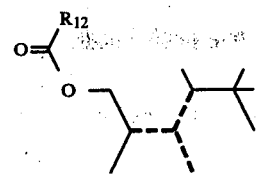

in the reaction mass may vary from about 2 moles per liter up to about 8 moles per liter with a concentration of 2–3 moles per liter of ester having the structure:

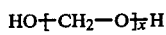

being preferred. The concentration of caustic is preferably double the concentration of ester. Thus, the concentration of caustic may vary from about 3 moles per liter up to about 10 moles per liter with a preferred concentration of caustic being about 5 moles per liter. The temperature of hydrolysis is preferably between about 50° C. up to about 80° C. with a hydrolysis temperature of 65° C. being preferred, at atmospheric pressure. Pressures above atmospheric pressure or below atmospheric pressure may be used for the hydrolysis reaction but using higher or lower pressures does not give rise to any advantage insofar as yield or conversion per unit time is concerned. Indeed, most economically, the reaction pressure for this hydrolysis reaction is preferably 1 atmosphere.

At the end of the hydrolysis reaction, the reaction mass may be appropriately worked up as by pH adjustment and fractional distillation thereby yielding the $C_{11}$ unsaturated alcohol having one of the structures:

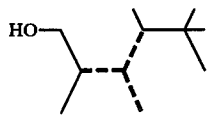

wherein one of the dashed lines represents a carbon-carbon double bond and each of the other of the dashed lines represent carbon-carbon single bonds.

If desired, the re-esterification reaction which may be represented thusly:

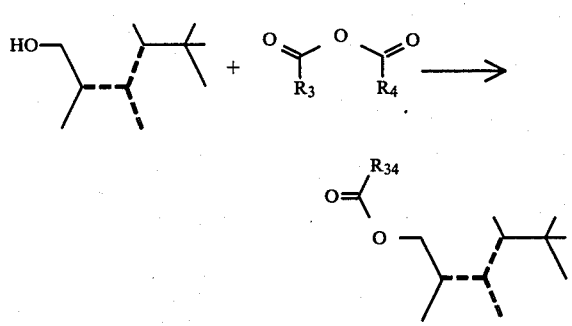

takes place wherein $R_3$ and $R_4$ are the same or different and each represents $C_1$–$C_3$ alkyl and $R_{34}$ represents one of $R_3$ or $R_4$ and represents $C_1$–$C_3$ alkyl. The re-esterification is usually carried out in order to create a higher yield of ester than that previously formable by means of the original reaction of acyl anhydride. Thus, if the initial reaction is carried out with acetic anhydride and it is ultimately desired to produce the propionate ester or the isobutyrate ester, then the most desirable route to take is to first form the acetate estate; then hydrolyze same and finally react the $C_{11}$ unsaturated alcohol with propionic anhydride according to the reaction:

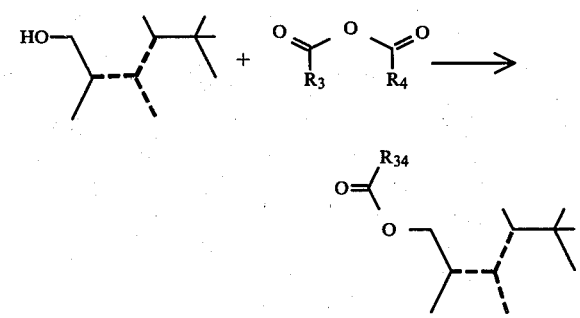

The mole ratio of acyl anhydride:$C_{11}$ unsaturated alcohol may vary from about 1:1 up to about 3:1 with a mole ratio of acyl anhydride, e.g., n-propionic anhydride:$C_{11}$ unsaturated alcohol of 2:1 being preferred.

The temperature of the esterification reaction, if carried out at atmospheric pressure, is preferably between 100° and 120° C. Higher pressures of reaction, that is, higher than atmospheric, are neither desired nor are they advantageous. By the same token, lower pressures of reaction are neither desired nor advantageous insofar as yield or conversion of reaction product.

At the end of the reaction, the reaction mass is worked up in the usual manner by first neutralizing the excess alkanoic acid anhydride with caustic and then neutralizing the reaction mass. The reaction mass is then distilled through a fractional distillation column to yield product acceptable from an organoleptic standpoint.

In carrying out the Prins reaction to form the cyclic ether, according to the reaction:

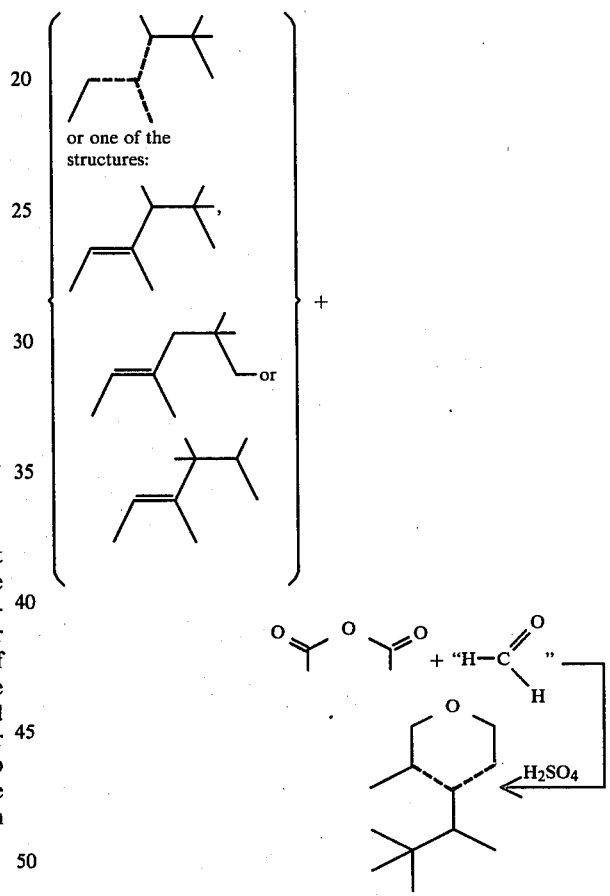

it is preferred that as a formaldehyde source, paraformaldehyde be used. Furthermore, it is preferred that the acid catalyst be concentrated sulfuric acid or concentrated phosphoric acid or concentrated paratoluene sulfonic acid or concentrated methane sulfonic acid.

The reaction may be carried out using a mole ratio of effective formaldehyde (as paraformaldehyde):diisoamylene of from 2:1 up to 1:2 with an effective mole ratio of formaldehyde:diisoamylene which is preferred being 2:1. The concentration of sulfuric acid or phosphoric acid or methane sulfonic acid or other protonic acid in the reaction mass, may vary from about 0.01 moles per liter up to about 1 mole per liter with a preferred concentration of protonic acid catalyst being from 0.1 up to 0.2 moles per liter. The mole ratio of acyl anhydride, preferably acetic anhydride:diisoamylene may vary from about 1:4 up to about 1:1 with a preferred mole ratio of acyl anhydride:diisoamylene being about 1:2. The reaction temperature may vary from about 50° C. up to about 120° C. but the preferred reaction temperature is 85°–95° C.

The reaction can be carried out at atmospheric pressure, super-atmospheric or sub-atmospheric pressure. No advantage exists either in conversion or yield when using super-atmospheric or sub-atmospheric pressure. Accordingly, it is most expeditious to utilize atmospheric pressures and a reaction temperature of from about 85° up to 95° C. in this reaction.

The following table sets forth the reaction products of my invention and the corresponding organoleptic properties:

TABLE I

| Structure of Reaction Product | Perfume Properties | Food Flavor Properties | Tobacco Flavor Properties |
|---|---|---|---|
| 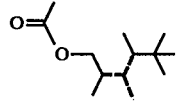<br>Mixture produced according to Example I wherein in each of the molecules, one of the dashed lines represents a carbon—carbon double bond and each of the other of the dashed lines represent carbon—carbon single bonds. | A woody, ionone-like, fruity and floral aroma with oriental nuances. | Raspberry seed aroma and taste. | An oriental, fruit, rum-like and Turkish tobacco-like aroma and taste prior to and on smoking in the main stream and the side stream. |
| 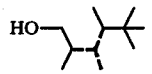<br>A mixture produced according to Example II wherein in each of the molecules, one of the dashed lines represents a carbon—carbon double bond and each of the other of the dashed lines represents carbon—carbon single bonds. | A woody, amber and floral aroma with minty and oriental-like nuances. | A minty and raspberry seed-like aroma and taste. | An oriental, Turkish tobacco-like aroma and taste both prior to and on smoking in the main stream and the side stream. |
| 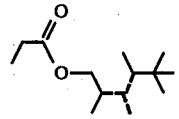<br>Mixture produced according to Example III wherein in each of the molecules of the mixture, one of the dashed lines represents a carbon—carbon double bond and each of the other of the dashed lines represents a carbon—carbon single bond. | A fruity, floral, woody and cedarwood aroma with amber and oriental topnotes. | An intense, strawberry/raspberry aroma and taste. | A fruity, rum-like aroma and taste both prior to and on smoking in the main stream and the side stream. |
| 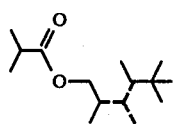<br>Mixture produced according to Example IV wherein in each of the molecules of the mixture, one of the dashed lines represents a | A fruity vanoris-like, peach-like, coriander-like, cedarwood and oriental aroma. | A sweet, floral, coriander-like, fruity, cedarwood and oriental aroma with a sweet, vanolin-like, floral, fruity, coriander-like, cedarwood and raisin taste causing it to be useful in raisin and rum flavors. | An oriental, fruity, rum-like, Turkish tobacco-like aroma and taste both prior to and on smoking in the main stream and the side stream. |

TABLE I-continued

| Structure of Reaction Product | Perfume Properties | Food Flavor Properties | Tobacco Flavor Properties |
|---|---|---|---|
| carbon—carbon double bond and each of the other of the dashed lines represent carbon—carbon single bonds. | | | |
| 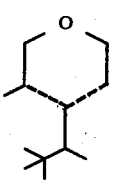<br>Mixture produced according to Example V wherein in each of the molecules of the mixture one of the dashed lines represents a carbon—carbon double bond and each of the other of the dashed lines represents carbon—carbon single bonds. | A woody, ionone-like, oriental and citrusy aroma with minty topnotes. | An intense, minty and citrus fruit and lemon peel aroma and taste. | A woody, cigar box, Turkish tobacco-like aroma and taste both prior to and on smoking in the main stream and the side stream. |

When the Prins reaction products produced according to the process of my invention are used as food flavor adjuvants, the nature of the co-ingredient included with the Prins reaction products used in formulating the product composition will also serve to alter, modify, augment or enhance the organoleptic characteristics of the ultimate foodstuff treated wherewith.

As used herein in regard to flavors, the terms "alter", "modify" and "augment" in their various forms means "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible non-toxic materials which have medicinal value such as cough syrups, couth drops, aspirin and chewable medicinal tablets.

The term "chewing gum" is intended to mean a composition which comprises a substantially water-insoluble chewable plastic gum base such as chicle, or substitutes therefor, including jelutong, guttakay rubber or certain comestible natural or synthetic resins or waxes. Incorporated with the gum base in admixture therewith may be plasticizers or softening agents, e.g., glycerine; and a flavoring composition which incorporates the Prins reaction products produced according to the process of my invention and, in addition, sweetening agents which may be sugars, including sucrose or dextrose and/or artificial sweeteners such as cyclamates or saccharine. Other optional ingredients may also be present.

Substances for use herein as co-ingredients or flavoring adjuvants are well known in the art for such use, being extensively described in the relevant literature. It is a requirement that any such material, be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may, in general, be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials, lipids, carbohydrates; starches, pectins and emulsifiers, e.g., mono- and diglycerides of fatty acids, skim milk powder, hexoses, pentoses, disaccharides, e.g. sucrose, corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like, starch modifiers such as peracetic acid, sodium chlorite, sodium hypochlorite, propylene oxide, succinic anhydride and the like, buffers and neutralizing agents, e.g., sodium acetate, ammonium bicarbonate, ammonion phosphate, citric acid, lactic acid, vinegar and the like, colorants, e.g. carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements; e.g., iron salts such as ferric phosphate, gerrous gluconate and the like, riboflavin, vitamins, zinc sources such as zinc chloride, zinc sulfate and the like.

Other flavorants and flavor intensifiers include organic acids, e.g. acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid and 2-methyl-3-pentenoic acid; ketones and aldehydes, e.g. acetaldehyde, acetophenone, acetone, acetyl methyl carbinol, acrolein, n-butanal, crotonal, diacetyl, 2-methyl butanal, $\beta,\beta$-dimethyl acrolein, methyl-n-amyl ketone, n-hexanal, 2-hexenal, isopentanal, hydrocinnanic aldehyde, cis-3-hexenal, 2-heptenal nonyl aldehyde, 4-(p-hydroxyphenyl)-2-butanone, alpha-ionone, beta-ionone, methyl-3-butanone, benzaldehyde, $\beta$-damascone, $\beta$-damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanol; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methyl-butyrate, ethyl propionate, ethyl salicylate, trans-2-hexenyl acetate, n-hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alpha-pinene; pyrazines, such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones, such as $\alpha$-nonalactone; sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, (i) be organoleptically compatible with the Prins reaction product(s) of my invention by not covering or spoiling the organoleptic properties (aroma and/or taste) thereof; (ii) be non-reactive with one or more of the Prins reaction products of my invention and (iii) be capable of providing an environment in which the Prins reaction product(s) of my invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste or chewing tobacco to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of Prins reaction product(s) or derivatives thereof of my invention employed in a particular instance can vary over a relatively wide range, depending upon the desired organoleptic effects to be achieved. Thus, correspondingly greater amounts would be necessary in those instances wherein the ultimate food composition to be flavored (e.g., a "raisin-rum cake") is relatively bland to the taste, whereas relatively minor quantities may suffice for purposes of enhancing the composition merely deficient in natural flavor or aroma, (e.g. when actual raisins and rum are present in the foodstuff such as the cake). The primary requirement is that the amount selected by effective, i.e. sufficient to alter, modify or enhance the orgaloleptic characteristics of the parent composition, whether foodstuff per se, chewing gum per se, medicinal product per se, toothpaste per se, chewing tobacco per se or flavoring composition.

The use of insufficient quantities of one or more Prins reaction products or Prins reaction product derivatives of my invention will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the content of the present invention consistent with the obtention of desired flavoring effects.

Thus, and with respect to ultimate food compositions, chewing gum compositions, medicinal product compositions, chewing tobacco compositions and toothpaste compositions, it is found that quantities of one or more Prins reaction products or Prins reaction product derivatives of my invention ranging from a small but effective amount, e.g., about 0.2 parts per million up to about 150 parts per million based on total food composition or chewing gum composition, or medicinal product composition or toothpaste composition or chewing tobacco composition are suitable. Concentrations in excess of the maximum quantity stated are not normally recommended since they fail to provide commensurate enhancement of organoleptic properties. In those instances where one or more Prins reaction products or Prins reaction product derivatives of my invention is added to the foodstuff as an integral component of a flavoring composition, it is, of course, essential that the total quantity of flavoring composition employed be sufficient to yield an effective concentration of one or more Prins reaction products or Prins reaction product derivatives of my invention in the foodstuff product.

Food flavoring compositions containing one or more of the compounds prepared in accordance with the present invention preferably contain one or more Prins reaction products or Prins reaction product derivatives in concentrations ranging from about 0.02% up to about 15% by weight of the total weight of said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing one or more of the Prins reaction products or Prins reaction product derivatives prepared in accordance with my invention with, for example, gum arabic, gum tragacanth, xanthan gum, carrageenan and the like, and thereafter spray-drying the resultant mixture whereby to obtain the particulate solid product. Pre-prepared flavor mixes in powder form, e.g. a fruit flavored or rum flavored powder mix are obtained by mixing the dried solid components, e.g., starch, sugar and the like and one or more Prins reaction products or Prins reaction product derivatives of my invention in a dry blender until the requisite degree of uniformity is achieved.

It is presently preferred to combine one or more Prins reaction product derivatives of my invention with at least one of the following adjuvants:
p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl Anthranilate;
5-Methyl furfural;
Isoamyl Acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-pentenal diethyl acetal;
$\beta$-Damascone (1-crotonyl-2,6,6-trimethylcyclohex-1-ene);
$\beta$-Damascenone (1-crotonyl-2,6,6-trimethylcyclohexa-1,3-diene);
Beta-cyclohomocitral (2,6,6-trimethylcyclohex-1-ene carboxaldehyde)
Isoamyl butyrate;
Cis-3-hexenol-1;
2-Methyl-2-pentenoic acid;
Elemecine (4-allyl-1,2,6-trimethoxybenzene);
Isoelemecine (4-propenyl-1,2,6-trimethoxybenzene); and
2-(4-Hydroxy-4-methylpentyl) norbornadiene
rum essence
3-hydroxy butyric acid
2-hydroxy butyric acid
N-methyl anthranilate
cyclotene
ethyl cyclotene
n-propyl cyclotene
gin berry essence One or more Prins reaction products or Prins reaction product derivatives prepared in accordance with the process of my invention and one or more auxiliary perfume ingredients including, for example, alcohols other than the $C_{11}$ unsaturated alcohols of my invention, aldehydes, ketones, terpenic hydrocarbons, nitriles, esters other than the Prins reaction products of my invention, lactones, natural essential oils and synthetic essential oils may be admixed so that the combined odors of the individual components produce a pleasant and desired fragrance, particularly, and preferably, in rose fragrances. Such perfumed compositions usually contain (a) the main note or the "bouquet" or foundation stone of the composition; (b) modifiers which round off and accompany the main note; (c) fixatives which include odorous substances which lend a particular note to the perfume throughout all states of evaporation and substances which retard evaporation; and (d) topnotes which are usually low-boiling fresh-smelling materials.

In perfume compositions, it is the individual components which contribute to their particular olfactory characteristics, however, the overall sensory effect of the perfume composition will be at least the sum total of the effects of each of the ingredients. Thus, one or more Prins reactions products or Prins reaction product derivatives prepared in accordance with the process of my invention can be used to alter, modify, or enhance the aroma characteristics of a perfume composition, for example, by utilizing or moderating the olfactory reaction contributed by another ingredient in the composition.

The amount of one or more Prins reaction product or Prins reaction product derivative prepared in accordance with the process of my invention which will be effective in perfume compositions as well as in perfumed articles (e.g. anionic, nonionic, cationic or zwitterionic detergents, soaps and fabric softener compositions and articles) and colognes depends upon many factors including the other ingredients, their amounts and the effects which are desired. It has been found that perfume compositions containing as little as 0.01% of one or more Prins reaction products or Prins reaction product derivatives prepared in accordance with the process of my invention and less 50% of one or more of the Prins reaction products or Prins reaction product derivatives prepared in accordance with the process of my invention or even less (e.g., 0.005%) can be used to impart a woody, ionone-like, fruity, floral, amber, cedarwood-like, vanoris-like, peach, coriander-like, oriental citrusy and minty aroma to soaps, cosmetics, anionic, cationic, nonionic, or zwitterionic detergents, fabric softener compositions, fabric softener articles or other products. The amount employed can range up to 70% of the fragrance components and will depend on considerations of cost, nature of the end product, the effect desired on the finished product and the particular fragrance sought.

The following Example A sets forth means for synthesizing precursors for use in synthesizing the products of my invention. The following Examples I-V illustrate methods of my invention used to manufacture Prins reaction products and Prins reaction product derivatives of my invention. Examples subsequent to Example V serve to illustrate the organoleptic utilities of my invention of the Prins reaction products and Prins reaction product derivatives manufactured in accordance with the processes of Example I-V.

All parts and percentages given herein are by weight unless otherwise specified.

EXAMPLE A

PREPARATION OF DIISOAMYLENES

Reaction:

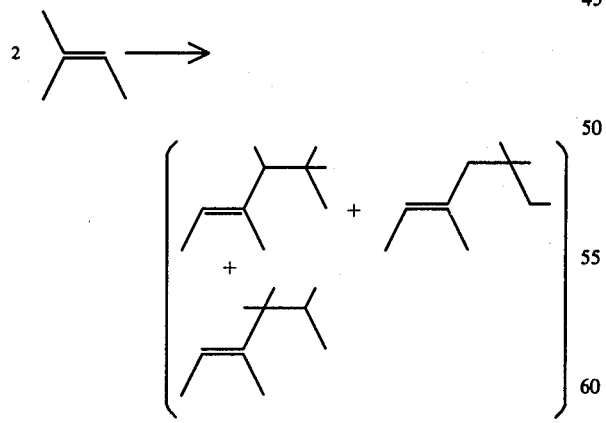

Diisoamylene is prepared according to one of the procedures set forth in the following references:

(i) Murphy & Lane, Ind. Eng. Chem., Prod. Res. Dev., Vol. 14, No. 3, 1975 p. 167 (Title: Oligomerization of 2-Methyl-2-Butene in Sulfuric Acid and Sulfuric-Phosphoric Acid Mixtures).

(ii) Whitmore & Mosher, Vol. 68, J. Am. Chem. Soc., February, 1946, p. 281 (Title: The Depolymerization of 3,4,5,5-Tetramethyl-2-hexene and 3,5,5-Trimethyl-2-heptane in Relation to the Dimerization of Isoamylenes).

(iii) Whitmore & Stahly, Vol. 67, J. Am. Chem. Soc., December, 1945, p. 2158 (Title: The Polymerization of Olefins. VIII The Polymerization of Olefins in Relation to Intramolecular Rearrangements. II).

(iv) U.S. Pat. No. 3,627,700 issued on Dec. 14, 1971, (Zuech).

(v) U.S. Pat. No. 3,538,181 issued on Nov. 3, 1970, (Banks).

(vi) U.S. Pat. No. 3,461,184 issued on Aug. 12, 1969 (Hay, et al).

(vii) Gurwitsch, Chemische Berichte, 1912, Vol. 2, p. 796 (Production of Di-isoamylene From Isoamylene Using Mercury Acetate Catalyst).

As an illustration, and not by way of limitation, the following example sets forth the preparation of diisoamylenes useful in producing the fragrance materials of my invention.

Over a period of ten hours, 2-methyl-2-butene is pumped through a 5'×⅝ (0.625 inch) tube packed with 15.0 grams of polystyrene sulfonic acid catalyst, at a temperature of 100° C. and at a pressure of 400 psig.

The resulting material was distilled in a fractionation column in order to separate the diisoamylene from the higher molecular weight polymers, which are formed during the reaction as by-products.

EXAMPLE I

PREPARATION OF ACETIC ACID ESTER MIXTURE OF $C_{11}$ ALCOHOLS

Reaction:

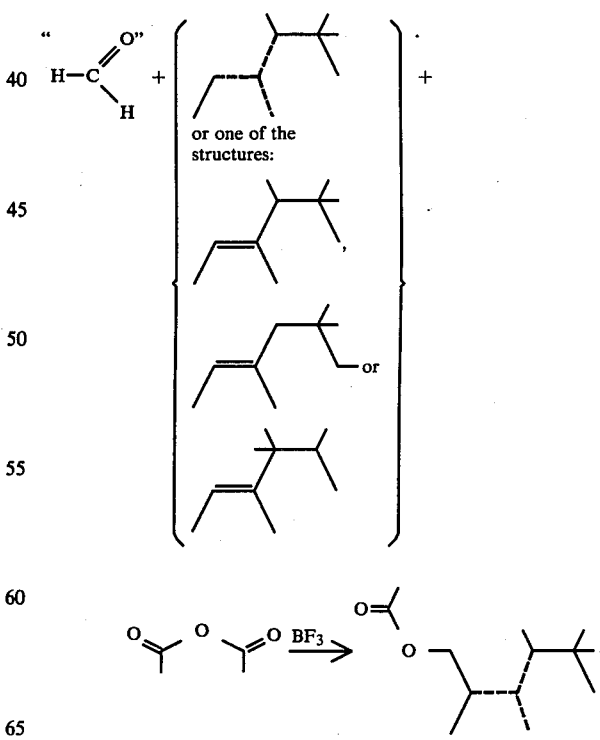

Into a 3 liter reaction flask equipped with reflux condenser, additional funnel, thermometer, stirrer and heating mantle is placed 1428 ml acetic anhydride (14 moles) and 25 ml boron trifluoride etherate (0.25 moles). The reaction mass is heated to 103° C. and while maintaining the reaction mass at 103°–108° C., over a period of 30 minutes, a mixture of 1600 ml diisoamylene prepared according to Example A (10.6 moles) and 324 grams of paraformaldehyde (10.8 moles of formaldehyde) is added slowly to the reaction mass. The reaction mass is then maintained at 85°–88° C. over a period of 2 hours. The reaction mass is then cooled and poured onto 2 liters of water and washed with 3 two-liter volumes of 5% sodium hydroxide followed by one 1500 ml portion of saturated sodium chloride. The reaction mass is then mixed with 400 ml methylene dichloride and dried over anhydrous sodium sulfate. The reaction mass is then distilled on a 2 inch packed column yielding the following fractions:

| Fraction Number | Vapor Temp. (°C.) | Liquid Temp. (°C.) | Pressure mm/Hg. | Weight of Fraction (g) |
| --- | --- | --- | --- | --- |
| 1 | 36 | 73 | 1.4 | 92 |
| 2 | 73 | 90 | .6 | 96 |
| 3 | 82 | 99 | .6 | 106 |
| 4 | 86 | 102 | .6 | 105 |
| 5 | 86 | 105 |  | 110 |
| 6 | 95 | 146 | 1.5 | 218 |
| 7 | 146 | 224 |  | 68 | and then redistilled on a 6 inch silver column packed with stones to yiled the following fractions:

| Fraction Number | Vapor Temp. (°C.) | Liquid Temp. (°C.) | Pressure mm/Hg. | Weight of Fraction (g) |
| --- | --- | --- | --- | --- |
| 1 | 30/89 | 89/96 | 4.4/4.4 | 34 |
| 2 | 78 | 93 | 2.0 | 93.5 |
| 3 | 94 | 75 | 2.0 | 84 |
| 4 | 77 | 95 | 1.6 | 75.7 |
| 5 | 80 | 97 | 1.6 | 93.8 |
| 6 | 80 | 100 | 1.6 | 90 |
| 7 | 81 | 104 | 1.6 | 75 |
| 8 | 84 | 115 | 1.6 | 45.3 |
| 9 | 138 | 181 | 1.6 | 50.8 |

EXAMPLE II

PREPARATION OF $C_{11}$ ALCOHOL

Reaction:

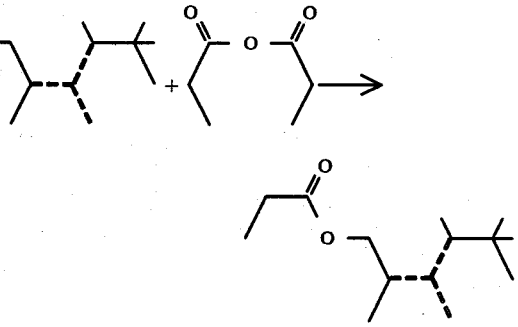

Into a 5 liter reaction flask equipped with stirrer, addition funnel, thermometer, nitrogen purge apparatus and heating mantle is placed:
1155 grams of the ester mixture prepared according to Example I
864 grams of 50% sodium hydroxide solution (10.8 moles)
1 liter water The reaction mass is heated at reflux with stirring for a period of 12 hours at 65°–67° C.

The reaction mass is then transferred to an open head separatory funnel and washed with one liter of saturated sodium chloride solution whereupon the pH of the oil layer is 6 and the pH of the aqueous layer is 12. The net weight of the oil layer is 1192 grams. The reaction mass is then distilled on a 2 inch stone packed column yielding the following fractions:

| Fraction Number | Vapor Temp. (°C.) | Liquid Temp. (°C.) | Pressure mm/Hg. | Weight of Fraction (g) |
| --- | --- | --- | --- | --- |
| 1 | 52/85 | 80/90 | 182/125 | 75 |
| 2 | 55 | 105 | 110 | 94 |
| 3 | 78 | 106 | 30 | 76 |
| 4 | 88 | 106 | 1 | 84 |
| 5 | 81 | 89 | 1 | 92 |
| 6 | 83 | 73 | 1 | 94 |
| 7 | 71 | 81 | 1 | 79 |
| 8 | 69 | 80 | 1 | 83 |
| 9 | 69 | 80 | 1 | 80 |
| 10 | 69 | 80 | 1 | 86 |
| 11 | 68 | 82 | 1 | 87 |
| 12 | 69 | 82 | 1 | 90 |
| 13 | 66 | 90 | 1 |  |
| 14 | 60 | 125 | 1 |  |

EXAMPLE III

FORMATION OF $C_{11}$ UNSATURATED ALCOHOL PROPIONATE

Reaction:

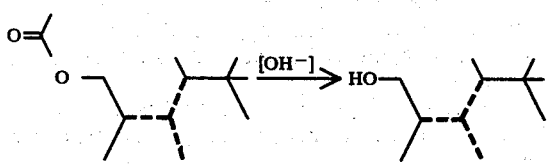

wherein in each of the compounds, one of the dashed lines represents a carbon-carbon double bond and each of the other of the dashed lines represent carbon-carbon single bonds.

Into a 1 liter reaction flask equipped with reflux condenser, addition funnel, thermometer, heating mantle and nitrogen feed line, is placed 400 ml (3.0 moles) of propionic anhydride. The propionic anhydride is heated to 110° C. and through the addition funnel is added 225 grams (1.5 moles) of the alcohol produced according to Example II. The reaction mass is maintained at 110° C. for a period of a half hour during the addition. At the completion of the addition (after a half hour), 20 ml of 50% sodium hydroxide and 80 ml water is added to the reaction mass. The reaction mass is stirred for an additional half hour at 110° C.

The reaction mass is transferred to an open head separatory flask containing 2 liters of water. Two phases now exist; an aqueous phase and an organic phase. The organic phase is washed with 100 ml 5% sodium hydroxide. The oil phase is then washed with 100 ml saturated sodium chloride solution so that the pH is 6. The reaction mass is then distilled on a 1 inch stone packed column yielding the following fractions:

| Fraction Number | Vapor Temp. (°C.) | Liquid Temp. (°C.) | Pressure mm/Hg. | Weight of Fraction (g) |
|---|---|---|---|---|
| 1 | 49/169 | 95/120 | 78 | 43 |
| 2 | 98 | 106 | 1 | 55 |
| 3 | 90 | 100 | 1 | 46 |
| 4 | 85 | 98 | 1 | 45 |
| 5 | 83 | 89 | 1 | 47 |
| 6 | 84 | 99 | 1 | 56 |
| 7 | 84 | 99 | 1 | 50 |
| 8 | 66 | 143 | 1 | 40 |
| 9 | 55 | 170 | 1 | |

EXAMPLE IV

PREPARATION OF ISOBUTYRIC ACID ESTER OF $C_{11}$ ALCOHOL

Reaction:

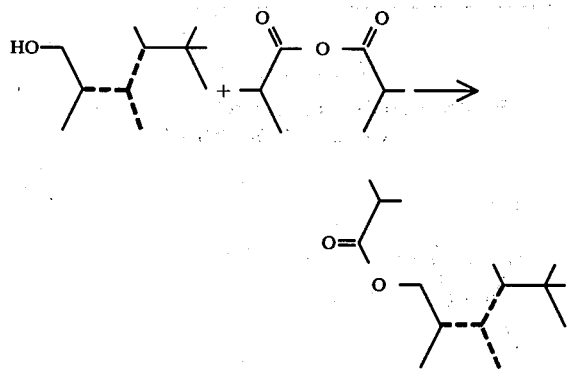

Into a 1 liter reaction flask equipped with reflux condenser, addition funnel, thermometer, heating mantle, gas bubbler and nitrogen purge apparatus, is placed 475 grams of isobutyric anhydride. The isobutyric anhydride is heated to 110° C. with stirring. Over a period of 1.5 hours, the $C_{11}$ alcohol mixture produced according to Example II, 255 grams, is added to the propionic anhydride. At the end of the addition of the $C_{11}$ alcohol, the reaction mass is heated for another 30 minutes at 110° C. The reaction mass is then admixed with 20 ml 50% sodium hydroxide and 80 ml water. The reaction mass is then transferred to a separatory funnel containing 1 liter of water. The reaction mass separates into an organic phase and an aqueous phase. The organic phase is washed with two 200 ml portions of water and stirred for 15 minutes. The organic phase is then washed with 5% sodium hydroxide until a pH of 6.

The reaction mass is then distilled on a 2 inch stone packed column yielding the following fractions:

| Fraction Number | Vapor Temp. (°C.) | Liquid Temp. (°C.) | Pressure mm/Hg. | Weight of Fraction (g) |
|---|---|---|---|---|
| 1 | 34/42 | 55/68 | .1 | 76 |
| 2 | 69 | 91 | .1 | 77 |
| 3 | 80 | 95 | .1 | 88 |
| 4 | 69 | 90 | .1 | 90 |
| 5 | 67 | 113 | .1 | 75 |
| 6 | 68 | 165 | .1 | 12 |

EXAMPLE V(A)

PRODUCTION OF REACTION PRODUCT OF DIISOAMYLENE WITH FORMALDEHYDE AND ACETIC ANHYDRIDE IN THE PRESENCE OF SULFURIC ACID CATALYST

Reaction:

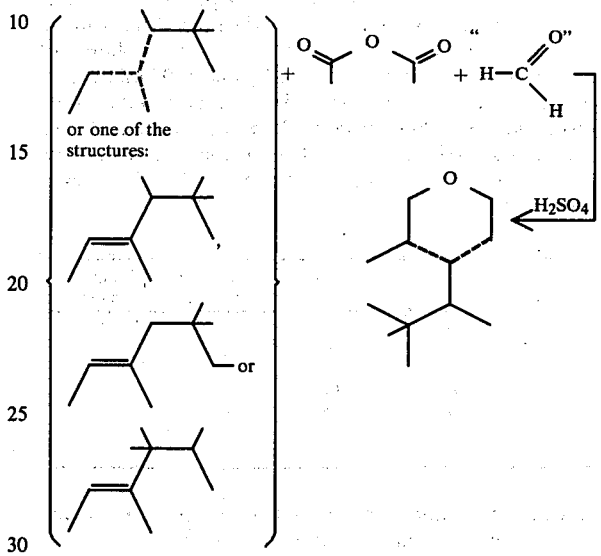

Into a 12 liter, 3 neck reaction flask equipped with stirrer, thermometer, reflux condenser and addition funnel, is placed 3,400 ml glacial acetic acid; 1,040 grams acetic anhydride followed by 1,200 grams of paraformaldehyde (powder) and 40 grams of concentrated (93%) sulfuric acid. The resulting mixture is heated to 90° C. Dropwise, over a period of 2 hours while maintaining the reaction temperature at 90° C., 2,800 grams (4 liters) of diisoamylene prepared according to Example A is added to the reaction mass. The reaction mass is then stirred for an additional 1 hour at 90° C.

The reaction mass is then cooled to room temperature and poured into 2 liters of water. The organic layer is separated from the resultant aqueous layer and the organic layer is washed as follows:

One 1 liter portion of water
Two liters of 12.5% sodium hydroxide solution
Two 1 liter portions of saturated sodium chloride solution The resulting organic layer is then dried over anhydrous magnesium sulfate, filtered, and stripped of solvent.

The resulting concentrate is then fractionally distilled on a 2 inch stone packed column yielding the following distillation fractions and at the following conditions:

| Fraction Number | Vapor Temp. (°C.) | Liquid Temp. (°C.) | Pressure mm/Hg. | Weight of Fraction (g) |
|---|---|---|---|---|
| 1 | 32/45 | 52/59 | 3.0/2.0 | 330 |
| 2 | 62 | 75 | 2.0 | 352 |
| 3 | | | | 377 |
| 4 | 81 | 95 | 2.0 | 405 |
| 5 | 90 | 105 | 2.0 | 398 |
| 6 | 95 | 111 | 2.0 | 404 |
| 7 | 101 | 120 | 2.0 | 369 |

The resulting product is then redistilled (bulked fractions 2, 3, 4, 5, 6 and 7) on a Goodloe column yielding the following fractions:

| Fraction Number | Vapor Temp. (°C.) | Liquid Temp. (°C.) | Pressure mm/Hg. | Weight of Fraction (g) |
|---|---|---|---|---|
| 1 | 43/67 | 97/90 | 6 | 78 |
| 2 | 73 | 93 | 6 | 73 |
| 3 | 76 | 93 | 6 | 45 |
| 4 | 76 | 93 | 6 | 79 |
| 5 | 81 | 95 | 6 | 33 |
| 6 | 82 | 95 | 6 | 91 |
| 7 | 81 | 95 | 6 | 101 |
| 8 | 81 | 95 | 6 | 78 |
| 9 | 65 | 92 | 3 | 79 |
| 10 | 65 | 92 | 3 | 75 |
| 11 | 63 | 92 | 3 | 86 |
| 12 | 63 | 93 | 3 | 97 |
| 13 | 63 | 93 | 3 | 97 |
| 14 | 63 | 94 | 3 | 97 |
| 15 | 63 | 97 | 3 | 108 |
| 16 | 63 | 98 | 3 | 78 |
| 17 | 63 | 101 | 3 | 94 |
| 18 | 66 | 104 | 3 | 44 |
| 19 | 68 | 108 | 3 | 64 |
| 20 | 69 | 115 | 3 | 70 |
| 21 | 74 | 130 | 3 | 52 |
| 22 | 85 | 135 | 3 | 71 |
| 23 | 100 | 136 | 3 | 58 |
| 24 | 110 | 147 | 3 | 97 |
| 25 | 118 | 225 | 3 | 66 |

EXAMPLE V(B)

HYDROLYSIS OF CYCLIC MATERIAL PREPARED ACCORDING TO EXAMPLE V(A)

Reaction:

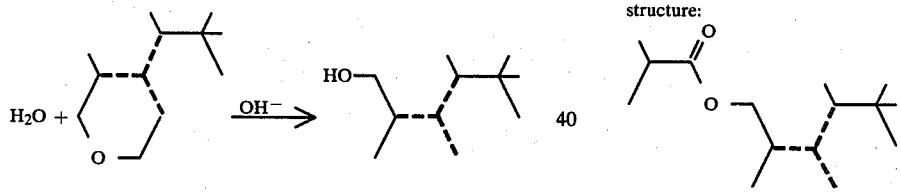

Into a 5 liter reaction flask equipped with thermometer, stirrer and reflux condenser is charged:
1,400 grams of the cyclic ether prepared according to Example V(A)
1,046 grams of 50% aqueous sodium hydroxide
100 ml water
5 grams of Aliquat ® 336 (cetyl trimethyl ammonium chloride manufactured by the General Mills Chemical Company of Minneapolis, Minn.)

The reaction mass is heated to reflux and maintained at reflux for a period of 8 hours (111° C.; atmospheric pressure). The reaction mass is subsequently cooled to room temperature and is now in two phases, an aqueous phase and an organic phase. The organic phase is removed and washed with saturated sodium chloride whereby the pH thereof is 7–8.

The crude oil is then removed and distilled on an 18 inch Goodlow, silver mirror distillation column yielding the following fractions:

| Fraction Number | Vapor Temp. (°C.) | Liquid Temp. (°C.) | Pressure mm/Hg. | Reflux Ratio | Weight of Fraction (g) |
|---|---|---|---|---|---|
| 1 | 88/89 | 60/60 | 4/2.4 | 4:1 | 68 |
| 2 | 60 | 90 | 2.4 | 4:1 | 97 |
| 3 | 60 | 90 | 2.4 | 4:1 | 93 |
| 4 | 60 | 90 | 2.0 | 4:1 | 85 |
| 5 | 53/58 | 89/90 | 1.7/1.4 | 4:1 | 88 |
| 6 | 58 | 91 | 1.2 | | 89 |
| 7 | 60 | 90 | 1.6 | 4:1 | 95 |
| 8 | 58 | 93 | 1.3 | 4:1 | 95 |
| 9 | 63 | 95 | 1.4 | 1:1 | 85 |
| 10 | 63 | 99 | 1.3 | 1:1 | 102 |
| 11 | 63 | 102 | 1.2 | 1:1 | 88 |
| 12 | 65 | 104 | 1.2 | 1:1 | 89 |
| 13 | 68 | 115 | 1.2 | 1:1 | 86 |
| 14 | 68 | 220 | 1.2 | 1:1 | 54 |

EXAMPLE VI

FLAVOR UTILITY OF ISOBUTYRIC ACID ESTER OF $C_{11}$ UNSATURATED ALCOHOL

The following raisin-rum flavor formulation is prepared:

| Ingredients | Parts by Weight |
|---|---|
| Natural rum essence | 48 |
| Citral | 2.8 |
| Carvone | 2.4 |
| Alpha-terpinene | 2.4 |
| Alpha-fenchyl alcohol | 3.8 |
| Geranyl acetone | 2.4 |
| Nootkatone | 5.4 |
| Neryl acetate | 3.6 |
| Natural lemon oil, terpineless | 12.3 |
| Mixture prepared according to Example IV containing the mixture defined according to the generic structure:<br />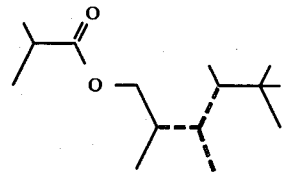<br />wherein in said mixture, one of the dashed lines represents a carbon-carbon double bond and each of the other of the dashed lines represent carbon-carbon single bonds. | 24.0 |
| Beta-hydroxy butyric acid | 4.2 |
| Natural grape essence | 2.0 |

The flavor formulation is compared to the same flavor formulation without the mixture of compounds defined according to the structure:

wherein the dashed lines are defined as above. Each of the formulations is compared at the rate of 50 parts per million in a standard vanilla ice cream. Each of the formulations is also compared separately in water at the rate of 5 parts per million. Side by side, the formulations with and without the compound defined according to the structure:

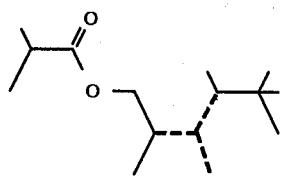

give rise to the conclusion that the flavor formulation containing the mixture of compounds defined according to the structure:

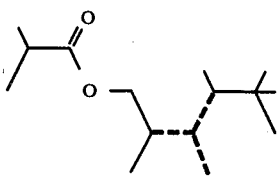

is greatly improved over the formulation without that mixture. The formulation containing the mixture defined according to the structure:

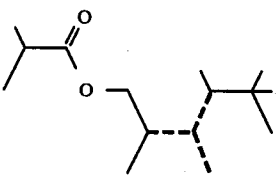

has a definite, more natural, more intense (five fold) rum-raisin nuance than the formulation without said mixture which is bland and relatively "synthetic tasting". In general, a bench panel of 5 members unanimously prefers the formulation containing the mixture of compounds defined according to the structure:

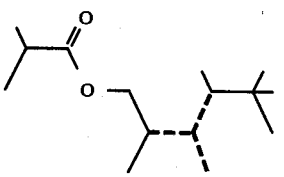

When the mixture of compounds defined according to the structure:

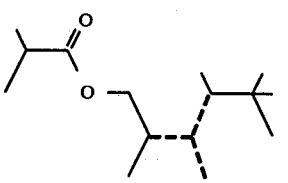

is replaced by the pure compound having the structure:

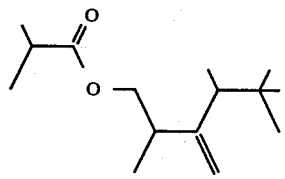

prepared by high pressure liquid chromatography separation of the foregoing mixture, the same result ensues.

EXAMPLE VII

A. Powder Flavor Formulation 20 grams of the flavor composition of Example VI is emulsified in a solution containing 300 grams of gum acacia and 70 grams water. The emulsion is spray-dried with a Bowen Lab Model Drier utilizing 260 c.f.m. of air with an inlet temperature of 500° F., an outlet temperature of 200° F. and a wheel speed of 50,000 rpm.

B. Sustained Release Flavor

| Ingredients | Parts by Weight |
| --- | --- |
| Liquid lemon flavor of Example VI | 20 |
| Propylene glycol | 9 |
| Cab-O-Sil ® M-5 (Brand of Silica produced by the Cabot Corporation of 125 High Street, Boston, Mass. 02110 Physical properties: Surface area: 200 m²/gm Nominal particle size 0.012 microns Density: 2.3 lbs/cu. ft.) | 5.00 |

The Cab-O-Sil ® is dispersed in the liquid rum-raisin flavor composition of Example VI with vigorous stirring, thereby resulting in a viscous liquid. 71 parts by weight of the powder flavor composition of Part A, supra, is then blended into the said viscous liquid, with stirring, at 25° C., for a period of 30 minutes resulting in a dry, free-flowing sustained release flavor powder.

EXAMPLE VIII 10 parts by weight of 50 Bloom pigskin gelatin is added to 90 parts by weight of water at a temperature of 150° F. The mixture is agitated until the gelatin is completely dissolved and the solution is cooled to 120° F. 20 parts by weight of the liquid flavor composition of Example VI is added to the solution which is then homogenized to form an emulsion having particle size typically in the range of 2-5 microns. This material is kept at 120° F. under which conditions the gelatin will not jell.

Coacervation is induced by adding, slowly and uniformly 40 parts by weight of a 20% aqueous solution of sodium sulfate. During coacervation, the gelatin molecules are deposited uniformly about each oil droplet as a nucleus.

Gelation is effected by pouring the heated coacervate mixture into 1,000 parts by weight of 7% aqueous solution of sodium sulfate at 65° F. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE IX

CHEWING GUM

100 Parts by weight of chicle are mixed with 4 parts by weight of the flavor prepared in accordance with Example VII. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting "rum-raisin" flavor.

EXAMPLE X

CHEWING GUM

100 Parts by weight of chicle are mixed with 18 parts by weight of the flavor prepared in accordance with Example VII. 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting rum-raisin flavor.

EXAMPLE XI

TOOTHPASTE FORMULATION

The following separate groups of ingredients are prepared:

| Parts by Weight | Ingredient |
|---|---|
| Group "A" | |
| 30.200 | Glycerine |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N—Lauroyl Sarcosinate (foaming agent) |
| Group "D" | |
| 1.200 | Flavor Material of Example VII |
| 100.00 | (Total) |

PROCEDURE:
1. The ingredients in Group "A" are stirred and heated in a steam jacketed kettle to 160° F.
2. Stirring is continued for an additional three to five minutes to form a homogeneous gel
3. The powders of Group "B" are added to the gel, while mixing, until a homogeneous paste is formed
4. With stirring, the flavor of "D" is added and lastly the sodium n-lauroyl sarcosinate
5. The resultant slurry is then blended for one hour. The completed paste is then transferred to a three roller mill and then homogenized, and finally tubed.

The resulting toothpaste when used in a normal toothbrushing procedure yields a pleasant rum-raisin flavor of constant strong intensity throughout said procedure (1–1.5 minutes).

EXAMPLE XII

CHEWABLE VITAMIN TABLETS

The flavor material produced according to the process of Example VII is added to a Chewable Vitamin Tablet Formulation at a rate of 10 gm/Kg which chewable vitamin tablet formulation is prepared as follows:

In a Hobart Mixer, the following materials are blended to homogeneity:

| | Gms/1000 Tablets |
|---|---|
| Vitamin C (ascorbic acid) as ascorbic acid-sodium mixture 1:1 | 70.00 |
| Vitamin $B_1$ (thiamine mononitrate) as Rocoat ® thiamine mononitrate 33⅓% (Hoffman La Roche) | 4.0 |
| Vitamin $B_2$ (riboflavin) as Rocoat ® riboflavin 33⅓% | 5.00 |
| Vitamin $B_6$ (pyridoxine Hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Flavor of Example VII | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 G dry Vitamin A acetate and 0.6 g Vitamin D are then added as beadlets. The entire blend is then compressed using concave punches at 0.5 g each.

Chewing of the resultant tablets yields a pleasant, long-lasting, consistently strong rum-raisin flavor with a tropical fruit-like background for a period of 12 minutes.

What is claimed is:

1. A process for augmenting or enhancing the aroma or taste of a foodstuff or chewing gum comprising the step of adding to said footstuff or chewing gum from about 0.2 parts per million up to about 150 parts per million based on total foodstuff composition or chewing gum composition of a mixture of compounds defined according to the structure:

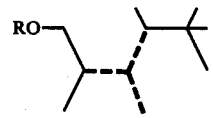

wherein R represents hydrogen or $C_2$–$C_4$ acyl and wherein in each of the compounds of the mixture, one of the dashed lines is a carbon-carbon double bond and each of the other of the dashed lines are carbon-carbon single bonds.

2. The process of claim 1 wherein R is n-propionyl.
3. The process of claim 1 wherein R is isobutyryl.
4. The process of claim 1 wherein R is acetyl.
5. The process of claim 1 wherein R is hydrogen.
6. A process for augmenting or enhancing the aroma or taste of a foodstuff or chewing gum composition comprising the step of adding to said foodstuff or chewing gum composition from about 0.2 parts per million up to about 150 parts per million based on total food composition or a chewing gum composition of a mixture of compounds defined according to the structure:

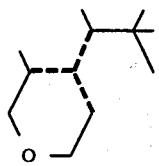

wherein in the mixture in each of the molecules one of the dashed lines represents a carbon-carbon double bond and each of the other of the dashed lines represent carbon-carbon single bonds.

7. A process for augmenting or enhancing the aroma or taste of a foodstuff or chewing gum composition comprising the step of adding to said foodstuff or chewing gum composition from about 0.2 parts per million up to about 150 parts per million based on total food composition or chewing gum composition of the compound defined according to the structure:

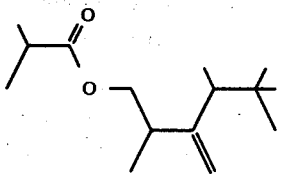

8. A process for augmenting or enhancing the aroma or taste of a foodstuff or chewing gum comprising the step of adding to said foodstuff or chewing gum from about 0.2 parts per million up to about 150 parts per million based on the total food composition or chewing gum composition of a mixture of compounds defined according to the structure:

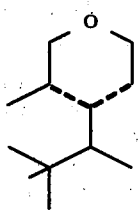

wherein in the mixture in each of the molecules of the mixture, one of the dashed lines represents a carbon-carbon double bond and the other of the dashed lines represents a carbon-carbon single bond.

* * * * *